(12) United States Patent
Cortright et al.

(10) Patent No.: US 6,455,742 B1
(45) Date of Patent: Sep. 24, 2002

(54) METHOD FOR CATALYTICALLY REDUCING CARBOXYLIC ACID GROUPS TO HYDROXYL GROUPS IN HYDROXYCARBOXYLIC ACIDS

(75) Inventors: Randy D. Cortright, Madison; James A. Dumesic, Verona, both of WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/634,825

(22) Filed: Aug. 9, 2000

Related U.S. Application Data

(63) Continuation-in-part of application No. 09/389,154, filed on Sep. 2, 1999, now abandoned.

(51) Int. Cl.[7] ............................................. C07C 29/141
(52) U.S. Cl. ........................................ 568/864; 502/158
(58) Field of Search .......................... 568/864; 502/158

(56) References Cited

U.S. PATENT DOCUMENTS

| | | | |
|---|---|---|---|
| 2,093,159 A | 9/1937 | Schmidt | 260/156 |
| 2,110,483 A | 3/1938 | Guyer | 260/156 |
| 2,275,152 A | 3/1942 | Lazier | 260/638 |
| 2,322,098 A | 6/1943 | Schmidt | 260/517 |
| 2,607,807 A | 8/1952 | Furd | 260/638 |
| 3,980,583 A | * 9/1976 | Mitchell et al. | 252/430 |
| 4,104,478 A | 8/1978 | Trivedi | 568/885 |
| 4,113,662 A | 9/1978 | Wall | 252/473 |
| 4,199,479 A | 4/1980 | Wilkes | 252/457 |
| 4,268,695 A | 5/1981 | Lange et al. | 568/864 |
| 4,361,710 A | 11/1982 | Weitz et al. | 568/864 |
| 4,386,219 A | 5/1983 | Merger et al. | 568/857 |
| 4,393,251 A | 7/1983 | Broecker et al. | 568/811 |
| 4,440,873 A | 4/1984 | Miyazaki et al. | 502/244 |
| 4,511,744 A | 4/1985 | Miyazaki et al. | 568/864 |
| 4,551,565 A | 11/1985 | Miyazaki et al. | 568/864 |
| 4,584,419 A | 4/1986 | Sharif et al. | 568/864 |
| 4,585,890 A | 4/1986 | Miyazaki et al. | 560/179 |
| 4,613,707 A | 9/1986 | Kouba et al. | 568/864 |
| 4,628,128 A | 12/1986 | Bartley | 568/864 |
| 4,647,551 A | 3/1987 | Miyazaki et al. | 502/200 |
| 4,649,226 A | 3/1987 | Poppelsdorf et al. | 568/864 |
| 4,652,685 A | 3/1987 | Cawse et al. | 568/864 |
| 4,751,334 A | 6/1988 | Turner et al. | 568/864 |
| 4,777,303 A | 10/1988 | Kitson et al. | 568/885 |
| 4,780,448 A | 10/1988 | Broecker et al. | 502/244 |
| 4,942,266 A | 7/1990 | Fleckenstein et al. | 568/864 |
| 5,030,771 A | 7/1991 | Fuhrmann et al. | 568/814 |
| 5,053,380 A | 10/1991 | Wegman et al. | 502/346 |
| 5,142,067 A | 8/1992 | Wegman et al. | 549/326 |
| 5,155,086 A | 10/1992 | Thakur et al. | 502/342 |
| 5,185,476 A | 2/1993 | Gustafson | 568/831 |
| 5,191,091 A | 3/1993 | Wegman et al. | 549/326 |
| 5,298,472 A | 3/1994 | Wegman et al. | 502/346 |
| 5,334,778 A | 8/1994 | Haas et al. | 568/862 |
| 5,345,005 A | 9/1994 | Thakur et al. | 568/885 |
| 5,387,753 A | 2/1995 | Scarlett et al. | 568/864 |
| 5,391,771 A | 2/1995 | Weyer et al. | 549/326 |
| 5,395,991 A | 3/1995 | Scarlett | 568/864 |
| 5,406,004 A | 4/1995 | Eastland et al. | 568/831 |
| 5,418,201 A | 5/1995 | Roberts et al. | 502/345 |
| 5,455,372 A | 10/1995 | Hirai et al. | 560/179 |
| 5,554,574 A | 9/1996 | Tsukuda et al. | 502/345 |
| 5,571,769 A | * 11/1996 | Gubitosa et al. | 502/244 |
| 5,696,303 A | 12/1997 | Darsow et al. | 568/864 |
| 5,710,349 A | 1/1998 | Furusaki et al. | 568/864 |
| 5,731,479 A | 3/1998 | Antons | 568/864 |
| 6,008,418 A | 12/1999 | Baur et al. | 568/853 |
| 6,037,504 A | 3/2000 | Darrow et al. | 568/864 |
| 6,100,410 A | 8/2000 | Tuck et al. | 549/325 |
| 6,191,321 B1 | 2/2001 | Forschner et al. | 568/864 |
| 6,191,322 B1 | 2/2001 | Bertola | 568/864 |
| 6,207,865 B1 | 3/2001 | Breitscheidel et al. | 568/705 |

FOREIGN PATENT DOCUMENTS

GB    2150560    7/1985

OTHER PUBLICATIONS

Surinder, P. C., Ullman's Encyclopedia of Industrial Chemistry, 5th Ed. (1990) vol. A15, pp. 97–105.

Datta, R., Kirk–Othmer Encyclopedia of Chemical Technology, 4th Edition (1995) vol. 13, pp. 1042–1062.

Zhang, Z. et al. "Propylene Glycol From Corn Derived Lactic Acid", 2000 Corn Utilization and Technology Conference, (Jun. 5–7, 2000), p. 211.

Carnahan, J.E., et al., "Ruthenium–catalysed hydrogenation of acids to alcohols," Journal of the American Chemical Society, vol. 77, No. 14, Jul. 1955, pp. 3766–3768; published by American Chemical Society.

* cited by examiner

*Primary Examiner*—Peter O'Sullivan
(74) *Attorney, Agent, or Firm*—Foley & Lardner

(57) ABSTRACT

A method for catalytically reducing the carboxylic acid group of hydroxycarboxylic acids to a hydroxyl group is disclosed. An organic compound having an α-hydroxyl group and at least one carboxylic acid group is contacted with a catalyst in the presence of hydrogen to yield a reduced product having at least two hydroxyl groups, the carboxylic acid group having been converted into one of the hydroxyl groups. The catalytic process may be conducted at hydrogen pressures of less than about 50 atm and is particularly suited for converting (α-hydroxycarboxylic acids, such as lactic acid or glycolic acid, to 1,2-dihydroxy alkanes, such as 1,2-propanediol or ethylene glycol, using zero valent copper. The catalyst may be supported on silica, and the hydroxyl groups on the silica may be capped with hydrophobic groups including alkyl groups and silanes, such as trialkylsilanes.

25 Claims, 2 Drawing Sheets

METHOD FOR CATALYTICALLY REDUCING CARBOXYLIC ACID GROUPS TO HYDROXYL GROUPS IN HYDROXYCARBOXYLIC ACIDS

CROSS REFERENCE TO RELATED APPLICATION

This application claims priority as a continuation-in-part application of U.S. Ser. No. 09/389,154, filed Sep. 2, 1999, now abandoned the complete disclosure of which is incorporated by reference.

This invention was made with United States government support awarded by the following agency: EPA Grant No. R825370. The United States government has certain rights in this invention.

FIELD OF THE INVENTION

This invention pertains generally to the field of catalytic hydrogenation, and more particularly relates to the catalytic hydrogenation of carboxylic acid groups to hydroxyl groups in hydroxycarboxylic acids.

BACKGROUND OF THE INVENTION

Dihydroxyalkanes such as ethylene glycol and 1,2-propanediol have uses in a wide variety of applications including as monomers in polyester resins; in antifreeze and deicing fluids; in the manufacture of food, drug and cosmetic products; and in liquid detergents. The demand for 1,2-propanediol has recently increased as it has become more common to substitute 1,2-propanediol for ethylene glycol in these applications.

1,2-propanediol, or propylene glycol, is currently produced by oxygenating propylene to produce the epoxide, propylene oxide. Propylene oxide is then typically reacted with water to form the desired 1,2-propanediol. Because this process begins with propylene, the price of the resulting 1,2-propanediol is linked to the change in the price of oil and other hydrocarbon non-renewable resources. There is a need for a method that produces dihydroxyalkanes from renewable resources such as plants.

It is well known that plants produce glucose from atmospheric carbon dioxide and sunlight in the process of photosynthesis. Because carbon dioxide is a greenhouse gas, any additional removal of the gas from the atmosphere helps to offset the increase in these gases by industrial emissions. It is well known that glucose may be obtained from a variety of natural sources such as corn starch, a natural product obtained from corn. Fermentation of glucose is well known to produce lactic acid, also known as α-hydroxypropanoic acid or 2-hydroxypropanoic acid. In fact, the majority of lactic acid currently produced is obtained through the fermentation of glucose.

Several types of fermentation exist for converting glucose to lactic acid. For example, in homolactic fermentation, the primary fermentation product is lactic acid, and various bacteria such as *Lactobacillus delbruckii, L. bulgaricus, L. Leichmanii, L. carsei,* and *L. salivarus* can be used. Surinder, P. C.; Ullman's Encyclopedia of Ind. Chem., 5$^{th}$ Edition (1990) Vol. A15, 100. In heterolactic fermentation, on the other hand, large amounts of other fermentation products such as acetic acid, ethanol, formic acid, and carbon dioxide may be produced depending on the materials and reaction conditions used. Id.

As non-renewable resources are diminished, the prices of materials obtained from such resources will undoubtedly increase. On the other hand, as advances in fermentation and separation technologies occur, the price of products obtained from fermentation processes will decrease. Thus, the price of lactic acid derived from natural, renewable resources should decrease as these advances are made. Furthermore, as production of glucose and lactic acid increases, the price of lactic acid should drop due to increased competition and economies of scale.

Conversion of the carboxylic acid functionality on lactic acid to a hydroxyl group produces 1,2-propanediol. Thus, if an economically feasible method were found that could effect this transformation, a route would be available for producing 1,2-propanediol from a renewable resource. What is thus needed, is an economical method for reducing the carboxylic acid group on hydroxycarboxylic acids to a hydroxyl group.

It has long been known that the catalytic hydrogenation of carboxylic acids is difficult. Thus, reductions of carboxylic acids are usually accomplished through a two-step process wherein the carboxylic acid is first converted into a more readily reducible derivative such as an ester or anhydride. Although the reduction of carboxylic acids has been described, such processes normally employ high hydrogen pressures and are also normally performed in the liquid phase. A process for directly converting a hydroxycarboxylic acid to a dihydroxyalkane, particularly a process which does so at lower pressures, would greatly reduce expenses associated with such a transformation as it would eliminate the unnecessary expenses associated with transforming the carboxylic acid group to a more readily reducible group.

Various patents disclose the reduction of carboxylic acid derivatives. For example, U.S. Pat. No. 2,093,159 issued to Schmidt discloses the reduction of esters to aldehydes and alcohols using activated copper, nickel, silver, zinc, cadmium, lead, or mixtures of these metals. The activating agents disclosed include metal compounds which give acids with oxygen such as chromium, molybdenum, tungsten, uranium, manganese, vanadium, or titanium in addition to compounds of the alkali, alkaline earth and rare earth metals. The patent discloses that metal catalyst activity can be achieved by depositing the metal catalyst on finely divided substrates such as fibrous asbestos, graphite, silica gel or metal powders. The temperatures for the catalytic reduction of esters is disclosed as ranging between 200° C. and 400° C., and Ni is disclosed as having superior reduction properties over copper.

The catalytic conversion of carboxylic acid anhydrides to alcohols is disclosed in U.S. Pat. No. 2,275,152 issued to Lazier. The catalysts disclosed for use in the reduction include mixtures of difficultly reducible oxides of hydrogenation metals such as chromites or chromates and oxides of magnesium, zinc, and manganese with readily reducible oxides of hydrogenation metals such as those of silver, cadmium, copper, lead, mercury, tin bismuth, iron, cobalt, and nickel. Hydrogen pressure in the process is greater than 10 atm, and operable temperatures are those in excess of 200° C.

A process for hydrogenating esters to alcohols with a cobalt-zinc-copper catalyst at temperatures between 100° C. and 350° C. and pressures ranging from 34 to 681 atm is disclosed in U.S. Pat. No. 4,113,662 issued to Wall. The patent discloses that the cobalt-zinc-copper catalyst is a highly effective ester hydrogenation catalyst in terms of activity, selectivity and stability.

A process for effecting hydrogenolysis of esters is disclosed in GB 2,150,560 issued to Kippax et al. The disclosed process includes contacting a vaporous mixture of an ester, hydrogen, and minor amounts of carbon dioxide with a catalyst consisting essentially of a reduced mixture of copper oxide and zinc oxide at a temperature ranging from about 150° C. up to about 240° C. and at a pressure ranging from about 4.9 to 14.8 atm. The addition of carbon dioxide was found to have a profound effect upon the activity of the Cu/Zn hydrogenation catalysts.

The catalytic conversion of carboxylic acids to alcohols has generally been described as more difficult than the conversion of esters to alcohols. Thus, the pressure and temperature required to effect the reduction of carboxylic acids have generally been higher than those required for reduction of esters and other carboxylic acid derivatives.

Catalytic hydrogenation of carboxylic acids and esters is disclosed in U.S. Pat. No. 2,110,483 issued to Guyer. The addition of iron is disclosed as improving the catalytic activity of catalysts, especially copper chromite which is referred to as a particularly suitable catalyst. Metals disclosed as having useful catalytic properties include copper, chromium, nickel, uranium, cobalt, zinc, cadmium, molybdenum, tungsten, and vanadium. The process can be carried out at pressures ranging from 50 to 400 atm and at temperatures ranging from 150° C. to 400° C.

The reduction of carboxylic acids is also disclosed in U.S. Pat. No. 2,322,098 issued to Schmidt. Suitable catalysts for the catalytic reduction performed at temperatures greater than 120° C. and pressures greater than 30 atm, preferably from 100 atm to 300 atm, include copper, nickel, iron, cobalt, and silver. Activated catalysts are disclosed as obtained by depositing the catalytic substance on large surface carriers such as fibrous asbestos, graphite, silica gel, or inert metal powders.

The liquid-phase ruthenium-catalyzed reduction of carboxylic acids is disclosed in U.S. Pat. No. 2,607,807 issued to Furd. The ruthenium-catalyzed reduction is conducted at pressures greater than 200 atm and at temperatures ranging from 90° C. to 300° C. The patent discloses that the catalytic ruthenium can be deposited on charcoal, and it specifies that the reduction can be performed in batch, semi-batch, or continuous processes.

The liquid-phase reduction of optically active carboxylic acids to optically active alcohols is disclosed in U.S. Pat. No. 5,731,479 issued to Antons. The ruthenium catalyzed reduction is conducted at temperatures ranging from 50° C. to 150° C. Although the reduction can purportedly be carried out at pressures ranging from 5 to 250 atm, the pressure ranges from only 100 to 200 atm in each of the examples provided.

The reduction of carboxylic acids to alcohols using rhenium is disclosed in U.S. Pat. No. 4,104,478 issued to Trivedi. The liquid-phase reduction is accomplished at pressures greater than 20 atm and temperatures ranging from 170° C. to 250° C. using rhenium black in combination with ruthenium, rhodium, platinum, or palladium, and the catalysts may be supported. There is no disclosure that the reduction can be performed on carboxylic acids containing hydroxyl groups.

The reduction of carboxylic acids, ketones, and aldehydes is described in U.S. Pat. No. 4,613,707 issued to Kouba et al. The reduction is accomplished with copper aluminum borate at pressures ranging from 68 atm to 340 atm and temperatures ranging from 100° C. to 300° C.

The reduction of $C_2$ to $C_{12}$ carboxylic acids at elevated temperatures and pressures using a catalyst with a first component which is either molybdenum or tungsten and a second component which is a noble metal of Group VIII is disclosed in U.S. Pat. No. 4,777,303 issued to Kitson et al. The two-component catalyst may be supported on graphitized carbons, graphites, silicas, aluminas, and silica/aluminas. There is no disclosure that the process can be used to reduce hydroxycarboxylic acids to dihydroxyalkanes.

Thus, a need remains for a low pressure method of converting the carboxylic acid functionality of hydroxycarboxylic acids to hydroxyl groups. More specifically, a need remains for a method for reducing the carboxylic acid functionality of α-hydroxycarboxylic acids such as lactic acid to a hydroxyl group such that 1,2-dihydroxyalkanes are produced.

SUMMARY OF THE INVENTION

The present invention provides a catalytic process for reducing the carboxylic acid group of hydroxycarboxylic acids, such as lactic acid, to produce a product having at least two hydroxyl groups, such as 1,2-propanediol. The present invention also provides supported hydrogenation catalysts and the products produced by the catalytic hydrogenation.

The present invention provides a catalytic process including contacting an organic compound, having at least one carboxylic acid group and an α-hydroxyl group bonded to a carbon atom adjacent to the carboxylic acid group, with a catalyst comprising zero valent copper in the presence of hydrogen to yield a reduced product. The carboxylic acid group is converted into a second hydroxyl group and the product thus has at least two hydroxyl groups.

In preferred processes, the organic compound is contacted with the catalyst and the hydrogen at a pressure of less than about 25 atm, more preferably at a pressure less than 10 atm and still more preferably at pressures from about 3 atm to about 7.1 atm and pressures from about 5.8 atm to about 7.1 atm. Other preferred processes are carried out at a hydrogen partial pressure of less than or about 4 atm while others are carried out at a hydrogen partial pressure of less than or about 1 atm.

In other preferred processes, the catalyst is a zero valent transition metal, and in more preferred processes, the transition metal is copper, silver, gold, cobalt, rhodium, iridium, nickel, molybdenum, palladium, platinum, iron, ruthenium, rhenium, osmium, or mixtures thereof. In most preferred processes, the catalyst is zero valent copper.

In some preferred processes, the organic compound is in the vapor phase when it contacts the catalyst, and in other preferred processes, the organic compound contacts the catalyst and hydrogen in the presence of water.

In preferred processes, the product is a 1,2-dihydroxylalkane, and in particularly preferred processes, the product is 1,2-propanediol, ethylene glycol, or mixtures of these. In other preferred processes, the organic compound catalytically reduced is lactic acid, glycolic acid, or mixtures of these.

In preferred processes, the catalyst is a supported catalyst, preferably supported on silica. In particularly preferred processes, the metal catalyst is deposited on a support and the amount of the metal catalyst on the support ranges from about 10 to about 20 weight percent. In particularly preferred processes, the catalyst is supported on silica having hydroxyl groups some of which are capped with hydrophobic groups. The hydrophobic groups are preferably silane or alkyl groups. Preferred alkyl groups include methyl, ethyl, propyl, butyl, pentyl, hexyl, or similar groups while preferred silane hydrophobic groups include trialkylsilanes such as trimethylsilane.

The catalytic process can be carried out at various temperatures such as from about 80° C. to about 400° C., but is preferably carried out at a temperature ranging from about 125° C. to about 250° C. In still other preferred processes, the catalytic reduction is carried out at temperatures of from about 180° C. to about 250° C.

The invention also provides a catalytic process including contacting an organic compound having a first hydroxyl group and at least one carboxylic acid group with a catalyst in the presence of hydrogen at a pressure of less than or about 4 atmospheres to yield a reduced product. The carboxylic acid group is converted into a second hydroxyl group and the product has at least two hydroxyl groups.

The invention provides a supported hydrogenation catalyst that includes a metal catalyst comprising copper. The metal catalyst is supported on silica, the silica having hydroxyl groups, some of which are capped with a hydrophobic group.

In preferred embodiments, the metal catalyst consists essentially of copper. In other preferred embodiments, the hydrophobic groups are alkyl groups or silanes such as those recited above. In still other preferred catalysts, the copper is obtained from copper nitrate.

Further features, and advantages of the present invention will be apparent from the following detailed description.

BRIEF DESCRIPTION OF THE DRAWINGS

The preferred exemplary embodiment of the invention will hereinafter be described in conjunction with the appended drawings, wherein like numerals denote like elements

DETAILED DESCRIPTION OF THE INVENTION

Figure 1:
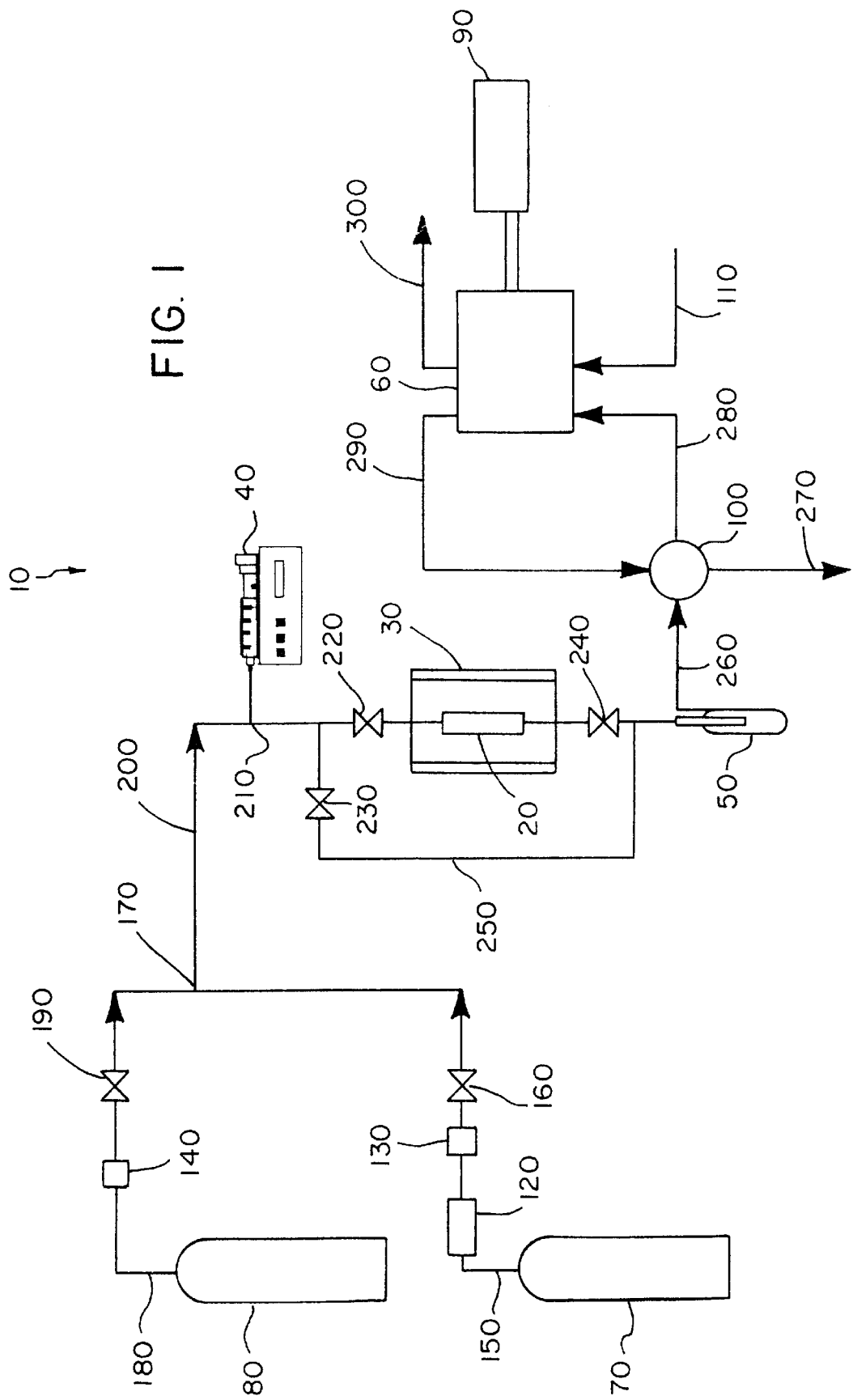
FIG. 1 is a schematic diagram of a kinetic apparatus used in the catalytic reduction of hydroxycarboxylic acids.

The term "about" as used herein in conjunction with a number refers to a range of from 90% to 110% of that number. For example a temperature of about 200° C. refers to a temperature ranging from 180° C. to 220° C.

Generally, the present invention provides a catalytic process for reducing a carboxylic acid group on an organic molecule to a hydroxyl group. The catalytic process is carried out by contacting an organic compound having a first hydroxyl group and at least one carboxylic acid group with a catalyst in the presence of hydrogen to yield a reduced product. During the catalytic process, at least one carboxylic acid group is converted into a second hydroxyl group. Thus, the reduced product has at least two hydroxyl groups.

The catalytic process may be conducted on dicarboxylic acids, but is more preferably carried out on monocarboxylic acids including, but not limited to, alkanoic and alkenoic acids. More preferably, the catalytic reduction is used to convert alkanoic acids into hydroxyalkanes.

Various functional groups may be present on the organic compound in addition to the carboxylic acid functionality. Preferably, the organic compound contains at least one hydroxyl functionality in addition to the carboxylic acid functionality. Thus, the organic compound is preferably a hydroxycarboxylic acid. Representative examples of hydroxycarboxylic acids include, but are not limited to, 2-hydroxyethanoic acid, 2-hydroxypropanoic acid, 3-hydroxypropanoic acid, 2-hydroxybutanoic acid, 3-hydroxybutanoic acid, 4-hydroxybutanoic acid, 3,4-dihydroxybutanoic acid, and others having more than 4 carbon atoms. More preferred organic compounds for use in the catalytic process include those with a hydroxyl group bonded to the carbon adjacent to the carboxylic acid group. Those skilled in the art will recognize that this class of organic compound may be referred to as α-hydroxycarboxylic acids because they have a hydroxy group bonded to the α carbon of the carboxylic acid. Representative members of this class of organic compound include, but are not limited to, glycolic acid (2-hydroxyethanoic acid), lactic acid (2-hydroxypropanoic acid), 2-hydroxybutanoic acid, 2-hydroxypentanoic acid, 2-hydroxyhexanoic acid, 2,3-dihydroxypropanoic acid, 2,4-dihydroxybutanoic acid, 2,5-dihydroxypentanoic acid, and 2,5-dihydroxyhexanoic acid. Lactic acid is an especially preferred organic compound that is reduced using the catalytic process of the invention. Another especially preferred organic compound that is reduced using the catalytic process is glycolic acid which can be catalytically reduced to ethylene glycol.

During the catalytic process, the carboxylic acid group of the organic compound is reduced to a hydroxyl group such that a hydroxyalkane or hydroxyalkene is formed. Preferably, the first hydroxyl group is retained during the catalytic hydrogenation such that the reduced product has at least two hydroxyl groups. Although the reduced product may have more than two hydroxyl groups, the preferred product of the reduction is a dihydroxyalkane. More preferably the reduced product is a dihydroxyalkane such as a 1,2-dihydroxyalkane. Most preferably, the reduced product is 1,2-dihydroxypropane. Thus, in a particularly preferred embodiment, the catalytic process includes contacting lactic acid with a catalyst in the presence of hydrogen such that 1,2-propanediol is formed. The α-hydroxycarboxylic acid to be reduced may be supplied in a relatively pure form in one preferred embodiment. However, it is also preferable that the α-hydroxycarboxylic acid be supplied as a component of an aqueous fermentation broth which is most preferably filtered or treated in some other fashion known to those skilled in the art to remove the majority of undissolved solids from the mixture. The feed mixture containing the α-hydroxycarboxylic acid may also be supplied with particulates and filtered prior to contacting the catalyst. Additionally, a filtered fermentation broth may be filtered again before the mixture is contacted with the catalyst. Although the α-hydroxycarboxylic acid preferably contacts the catalyst in the gas phase, it is also preferable to conduct the reduction by supplying the organic compound such that it contacts the catalyst in the liquid phase. In another particularly preferred embodiment, the catalytic process includes contacting glycolic acid with a catalyst in the presence of hydrogen such that ethylene glycol is formed.

The catalyst for use in the process of the present invention generally comprises a zero valent transition metal. Preferred transition metals for use in the process include copper, silver, gold, cobalt, rhodium, iridium, nickel, molybdenum, palladium, platinum, iron, ruthenium, rhenium, osmium, and mixtures of these metals. The most preferred transition metal for use in the catalytic hydrogenation process is zero valent copper as superior catalytic reduction has been achieved using catalysts and supported catalysts which contain only copper as the active metal catalyst. Thus, while other metals may be used, a preferred process is carried out using copper and supported copper catalysts as described below. It should be noted that not all copper catalysts work as well as the zero valent copper. For example, copper chromite does not catalyze the reduction as efficiently as those copper catalysts prepared from other materials. Preferred catalysts are prepared using copper salts such as, but not limited to, copper nitrate copper acetate, and copper hydroxide as described below. Most preferred catalysts are prepared using copper nitrate solutions. Preferably, the copper salts used will contain less than about 10%, or more preferably less than about 5%, and even more preferably less than 1% of a counterion containing a transition metal that will interfere with the catalytic activity of the copper such as copper chromite. Most preferably, a copper salt used to prepare the active catalysts will be free of counterions containing a transition metal that will interfere with the catalytic activity of the copper. The phrase "zero valent copper" is defined as copper in the metallic state which is typically obtained by reducing a copper salt such as the preferred salts described above with hydrogen. The phrase does not include copper catalysts prepared using only copper chromite as the source of copper. A catalyst containing zero valent copper may contain copper salts and still show good catalytic activity. Preferably however, a catalyst containing zero valent copper contains less than 5%, more preferably less than 2%, still more preferably less than 1%, and most preferably only traces to no unreduced salts of copper.

Although the catalyst may be used without any support, in preferred embodiments of the invention, a zero valent transition metal is deposited on a support. Various supports can be used. Such supports include, but are not limited to, graphite, silica, γ-alumina, zeolites, silicon nitride, zirconium dioxide, and titanium dioxide. Especially preferred catalysts for use in the catalytic processes include zero valent metals such as those described above supported on silica, such as Cab-O Sil™ fumed silica available from Cabot® Corporation (Boston, Mass.). Such supported catalysts are conveniently prepared by first impregnating the support with a salt solution of the intended catalyst. For example, silica may be stirred in a solution of copper nitrate followed by solvent removal. Next, the impregnated support is typically exposed to hydrogen at high temperatures, such as at 300° C., which effectively reduces the metal to its elemental state. In this manner, a supported catalyst comprising a zero valent transition metal, such as copper, and a support, such as silica, may be readily prepared. By altering the amount of metal salt used in proportion to the amount of silica, supported catalysts may be prepared with varying levels of metal supported on the catalyst. As noted, the amount of metal catalyst present in the supported catalyst may vary considerably. However, preferred supported catalysts are those which have the metal present in an amount ranging from about 10 to about 20 percent, more preferably ranging from about 10 to about 15 percent, based on the total weight of the supported catalyst. It should be noted that catalysts with as little as 5 percent (w/w) copper still show catalytic activity, and it is highly likely that catalyst activity could be detected at considerably lower levels.

Modification of the hydroxyl groups on silica affords a support that is particularly useful in the catalytic reduction of carboxylic acid functionalities. Thus, although unmodified fused silica such as Cab-O-Sil™ is an excellent support for use in the present invention, capping of at least some of the hydroxyl groups on the silica provides an alternative excellent support for use in the present invention. The hydroxyl groups of the silica are preferably capped with a hydrophobic group such as, but not limited to silanes and alkyl groups. Particularly suitable capping groups are alkyl groups such as, but not limited to, methyl, ethyl, propyl, butyl, pentyl, and hexyl groups. Mixtures of these alkyl groups may also be used as may mixtures of alkyl and silane groups. Another preferred type of capping group includes trialkylsilanes such as, but not limited to, trimethylsilane, triethylsilane, tripropylsilane, methyldiethylsilane, t-butyldimethylsilane, and triisopropylsilane. Trimethylsilane is an especially useful capping group for use in the present invention. Capping of the hydroxyl groups may be accomplished using conventional silylating or alkylating agents such as, but not limited to, trimethylchlorosilane, methyl iodide, t-butyldimethylsilyl chloride, and ethyl iodide.

Silica having capped hydroxyl groups may be loaded with a metal catalyst using the same methodology used to prepare uncapped supported catalysts as described above.

Although the catalytic process may be carried out in the liquid phase, it is preferable that the organic compound be in the vapor phase. The process is also highly versatile in that it may be carried out in a batch, semi-batch, or continuous manner. However, the catalytic reduction is preferably carried out in a continuous reaction by continuously passing the organic compound over a bed of the catalyst in the presence of hydrogen so that the organic compound contacts the catalyst and reacts with the hydrogen to afford the reduced product. Conventional equipment known to those skilled in the art may be used to effect the catalytic process. However, a preferred method includes the use of a kinetic apparatus such as that shown in FIG. 1.

As shown in FIG. 1, the kinetic apparatus 10 for use in the present invention generally includes a reactor 20 contained in a furnace 30; a means for introducing the carboxylic acid into the system such as a syringe pump 40; a trap 50 for removing condensables; a gas chromatograph (GC) 60; and a source of hydrogen such as a hydrogen cylinder 70. Other parts of the kinetic apparatus 10 typically include an inert gas source such as a helium cylinder 80; an integrator 90 for determining the area under the peaks obtained from GC 60; a sample valve 100; a carrier gas line 110 for use with GC 60; a deoxy unit 120 for removing trace amounts of oxygen from the hydrogen; and mass flow controllers 130 and 140 for allowing close control of mass flow of hydrogen and helium respectively.

In operation, gas from hydrogen cylinder 70 typically passes though a hydrogen line 150 before passing through deoxy unit 120. The amount of hydrogen gas flowing to junction 170 is controlled by mass flow controller 130 and valve 160. The flow of an inert gas, such as helium from helium cylinder 80, is controlled in a similar manner. Generally, helium from helium cylinder 80 flows through helium line 180 to mass flow controller 140 and then through valve 190 before reaching junction 170 where it is mixed with hydrogen. Of course one or both valves 160 and 190 may be shut to prevent one or more of the gases from entering the system.

After reaching junction 170, the gas or gas mixture flows through gas line 200 to junction 210 where the carboxylic acid to be reduced is introduced into the system such as by syringe pump 40. Valves 220 and 230 function to control the flow of the gas or gas mixture respectively through and/or around reactor 20. The carboxylic acid group is reduced to a hydroxyl functionality as the carboxylic acid contacts the catalyst in reactor 20 in the presence of hydrogen at a temperature determined by that of furnace 30. The product of the catalytic hydrogenation passes through valve 240 and into trap 50 which is typically immersed in liquid nitrogen or a mixture of dry ice and acetone to condense condensable reactants and products out of the product stream. The uncondensed gas and other materials then pass through line 260 to sample valve 100. Sample valve 100 is designed so that the gaseous uncondensed reaction mixture can be fed out of the system through exit line 270 or to the GC 60 for analysis through line 280. Some of the gas is then fed back to sample valve 100 through return line 290. The gas used for the GC analysis mixes with helium carrier gas entering the GC through carrier gas line 110 and then passes out of the system through exit line 300. Those skilled in the art will recognize that various other systems may be used in accordance with the present invention and that the kinetic apparatus described above represents only one such acceptable system.

The catalytic process according to the invention may produce other products in addition to that resulting solely from the conversion of the carboxylic acid group to a hydroxyl group. Some of these products include alcohols, carboxylic acids differing from the organic compound starting material, and aldehydes. Tables 1–8 illustrate some of the products obtained from the catalytic hydrogenation of lactic acid under varying conditions. Those skilled in the art will recognize that it is not required that all the organic compound react during the catalytic hydrogenation, and Tables 1–8 provide information regarding the conversion of lactic acid to various products under varying conditions.

As shown in Table 2, it has been discovered that the presence of water tends to increase both the percent conversion and the percent of dihydroxyalkane produced during catalytic processes. Thus, it is preferred that the organic compound be contacted with the catalyst and hydrogen in the presence of water. It should be recognized, however, that other solvents such as, but not limited to, alkanols and hydrocarbons may be used in the catalytic process.

The catalytic hydrogenation process necessarily requires that the organic compound contact the catalyst in the presence of hydrogen. The term "hydrogen" as used herein refers to $H_2$, $D_2$, H-D, H-T, D-T, and $T_2$ where "D" and "T" refer to deuterium and tritium. Other gases such as, but not limited to, nitrogen, helium, and argon may also be present in the catalytic hydrogenation process. The catalytic reduction of the organic compound can be accomplished at hydrogen pressures of up to 50 atm and higher. However, it has surprisingly been found that the reduction also proceeds at low hydrogen pressures of less than and about 1 atm. In some preferred processes, the hydrogen pressure is less than about 30 atm while in other preferred processes, the pressure is less than about 25 atm. In more preferred processes, the hydrogen pressure is less than about 10 atm, more preferably less than or about 7.1 atm, even more preferably less than or about 5.8 atm, less than or about 4.4 atm, or less than or about 3.0 or 2.0 atm. Preferred pressure ranges for the catalytic reduction include pressure from 10 atm to about 1 atm, more preferably from about 7.1 to about 2 atm, still more preferably from about 7.1 to about 3 atm, and most preferably from about 7.1 to about 5.8 atm. In other particularly preferred processes, the hydrogen partial pressure is less than or about 1 atm as this allows the process to be carried out without the use of apparatus adapted for high pressure. Any pressure range falling within 1 to 30 atm is preferred in catalytically converting the organic compound to the reduced product. The ability to perform this reduction at low pressures provides important economic and other advantages to this catalytic process. For example, the lower pressure required for the reduction reduces the expenses associated with high pressure equipment and lines.

The catalytic process may be performed at various temperatures as hydroxycarboxylic acids are reduced to dihydroxyalkanes at temperatures up to and including 400° C. The reduction may also be performed at temperatures as low as about 80° C. Preferably, however, catalytic reduction will be performed at temperatures ranging from about 125° C. to about 250° C. More preferred temperature ranges include all ranges and subcombinations within temperatures ranging from about 140° C. to about 220° C. as shown in Table 7. The reduction is even more preferably conducted at temperatures ranging from 160° C. to 210° C. Other preferred temperature ranges for catalytically reducing the organic compound to a dihydroxyalkane include temperatures ranging from about 180° C. to about 250° C., and more preferably temperatures ranging from 180° C. to 220° C. The reduction is most preferably conducted at temperatures ranging from about 180° C to 200° C.

EXAMPLES

Example 1

Preparation of a Supported Copper Hydrogenation Catalyst

Silica-supported copper catalysts were prepared using the incipient wetting technique. The following steps were used to prepare supported copper catalysts. First, Cab-O-Sil® EH-5 fumed silica available from Cabot® Corporation (Boston, Mass.) was dried at 120° C. Next a metal salt was impregnated on the fumed silica by dropwise addition of a copper nitrate hydrate solution in ethanol (approximately 1 gram of solution per gram of catalyst). Finally, the catalyst was prepared by flowing hydrogen over the impregnated support for 8 hours while maintaining the temperature at 300° C. The reduction of the catalyst was performed with a gas hourly space velocity of greater than 4000 $h^{-1}$.

Example 2

Effects of Copper Loading

Catalysts prepared using the method of Example 1 were loaded into a glass reactor, reduced for 8 hours at 300° C. in flowing hydrogen, and used for the vapor reduction of lactic acid at 1 atm at 200° C. The kinetic apparatus introduced 85% (w/w) lactic acid in water via a syringe pump to a heated line of flowing hydrogen. The reaction mixture was passed through a preheated section to vaporize the lactic acid solution, and it was then passed over the catalyst bed at 200° C. The molar ratio of lactic acid to water to hydrogen was 1.0:0.9:35. Condensable products were collected in a glass trap surrounded by liquid nitrogen. The non-condensable gases were analyzed via an online gas chromatograph (GC). The condensable products were weighed, diluted, and analyzed by GC. Table 1 shows the effects of copper loading on the conversion and selectivity of lactic acid reduction. The reaction pathway for the reduction of lactic acid to 1,2-propanediol is believed to proceed through the aldehyde, 2-hydroxypropanal. Other by-products that may form are n-propanol, isopropanol, and propanoic acid. Higher conversions are noted with increased copper content in the reactor as shown in Table 1. Unexpectedly, Table 1 shows that increasing the copper content also increases the selectivity of the desired products (1,2-propanediol and 2-hydroxypropanal) formed.

Example 3

Effects of Lactic Acid Concentration

The effect of lactic acid concentration on the reduction of hydroxy-carboxylic acids was investigated at 1 atm and at 200° C. over the 15% (w/w) silica-supported copper catalyst prepared using the method of Example 1. The kinetic apparatus introduced 21% (w/w) lactic acid in water via a syringe pump to a heated line of flowing hydrogen. The molar ratio of lactic acid to water to hydrogen under these conditions was 1.0:18:170. The results shown in Table 2 demonstrate that increasing the water concentration improves the selectivity of desired products formed.

Example 4
Stability of Copper on Silica

The activity of a 15% (w/w) silica-supported copper catalyst for the reduction of lactic acid was determined as a function of time. The supported catalyst was prepared according to the procedure set forth in Example 1. The reduction was conducted at 1 atm and 200° C. using the kinetic apparatus. Lactic acid (21% (w/w)) in water was injected via a syringe pump to a heated line of flowing hydrogen. The molar ratio of lactic acid to water to hydrogen under these conditions was 1.0:18:170. Table 3 demonstrates that the selectivity improves with time during the 5.5 hour duration of the experiment.

Example 5
Modification of Silica with Hydrophobic Capping Groups

The silica support was modified to reduce the amount of hydroxyl groups via capping with trimethylchlorosilane. In this procedure, Cab-O-Sil® EH-5 fumed silica was first refluxed in concentrated hydrochloric acid. It was then washed with distilled water and then with acetone. After drying, the activated silica was refluxed with sodium hydroxide. Next, the silica was washed with water and then with acetone. The silica was dried and then refluxed under a nitrogen atmosphere in a toluene/trimethylchlorosilane solution for 1 hour. The silica was then progressively washed with toluene and then water. After drying in a vacuum oven overnight, the silica was refluxed in water for 1 hour and then washed with acetone before drying. The dried, capped silica was next impregnated with a copper nitrate in ethanol solution and loaded into a reactor. Hydrogen was flowed over the resulting copper-impregnated trimethylsilyl-capped silica for 36 hours at 200° C. before reduction of a carboxylic acid was initiated.

Example 6
Reduction of Lactic Acid over Silica-Capped Supported Catalyst

The copper catalyst supported on silylated silica prepared in Example 5 was used to reduce lactic acid to 1,2-propanediol. The kinetic apparatus introduced 21% (w/w) lactic acid in water via a syringe pump to a heated line of flowing hydrogen at 1 atm. The molar ratio of lactic acid to water to hydrogen was 1.0:18:170. Table 4 shows that copper supported on capped silica has similar reactivity to copper supported on silica. Capping defunctionalizes the support and may have beneficial effects on the selectivity by decreasing side reactions such as dehydration, condensation, and polymerization reactions of lactic acid.

Example 7
Preparation of Catalysts on Other Supports

Following a procedure similar to that set forth in Example 1, $\gamma$-$Al_2O_3$, $SiN_4$, and $ZrO_2$ were impregnated using copper nitrate hydrate in ethanol. The resulting catalysts were reduced with flowing hydrogen at 300° C. for 8 hours before using them to reduce hydroxycarboxylic acids. These catalysts were used to convert 21% (w/w) lactic acid solution at 1 atm at a temperature of 200° C. The molar ratio of lactic acid to water to hydrogen was 1:18:170. Table 4 shows that the prepared supported catalysts also reduce lactic acid to 1,2-propanediol.

Example 8
Effects of Lactic Acid Weight Hourly Space Velocity

A supported catalyst (15% (w/w) copper on silica) produced using the method of Example 1 was loaded into a glass reactor and reduced for 8 hours at 300° C. in flowing hydrogen. The reduced catalyst was then used for the vapor reduction of lactic acid at 1 atm at a temperature of 200° C. The feed rate of 85% (w/w) lactic acid in water was altered to vary the weight hourly space velocity (WHSV) across the catalyst. Table 5 shows that decreasing the WHSV increases the observed conversion of lactic acid. Furthermore, Table 5 shows that higher selectivity in the production of 1,2-propanediol occurs with decreasing WHSV.

Example 9
Effect of Hydrogen Pressure

The same 15% (w/w) copper on silica catalyst used in Example 8 was used for the vapor reduction of lactic acid at 1 atm at a temperature of 200° C. The feed rate of 85% (w/w) lactic acid in water was set to achieve a WHSV of 0.02 $h^{-1}$ across the catalyst. The hydrogen concentration was varied by mixing inert helium in the gas stream. Table 6 shows that decreasing the hydrogen partial pressure decreases both the conversion of the lactic acid and the selectivity of 1,2-propanediol formed.

Example 10
Effect of Temperature

The same 15% (w/w) copper on silica catalyst used in Example 9 was used for the vapor reduction of lactic acid at 1 atm at various temperatures with a WHSV of 0.02 $h^{-1}$ and a hydrogen partial pressure of 0.99 atm. Table 7 shows that the lactic acid conversion increases and the 1,2-propanediol selectivity decreases with increasing temperature under these conditions. Activation energies for the production of 1,2-propanediol, propanoic acid, and 2-hydroxypropanal were determined to be 37, 66, and 51 kJ/mol respectively. Combining the results of Examples 8, 9, and 10 indicates that higher selectivities for 1,2-propanediol production are expected at lower temperatures and higher hydrogen partial pressures.

Example 11
Reduction of Glycolic Acid

The copper catalyst supported on silylated silica prepared in Example 5 is used to reduce glycolic acid to ethylene glycol. Similarly, a 15% (w/w) copper on silica catalyst prepared according to Example 1 is used to reduce glycolic acid to ethylene glycol. Both reductions are carried out at a temperature of 180° C. The kinetic apparatus introduces 21% (w/w) glycolic acid in water via a syringe pump to a heated line of flowing hydrogen at 1 atm. The molar ratio of glycolic acid to water to hydrogen is 1.0:18:170. Ethylene glycol is produced using either the copper supported on capped silica or the 15% (w/w) copper on silica catalysts.

Example 12
Reduction of 2-Hydroxybutanoic Acid

The copper catalyst supported on silylated silica prepared in Example 5 is used to reduce 2-hydroxybutanoic acid to 1,2-dihydroxybutane. Similarly, a 15% (w/w) copper on silica catalyst prepared according to Example 1 is used to reduce 2-hydroxybutanoic acid to 1,2-dihydroxybutane. Both reductions are carried out at a temperature of 180° C. The kinetic apparatus introduces 21% (w/w) 2-hydroxybutanoic acid in water via a syringe pump to a heated line of flowing hydrogen at 1 atm. The molar ratio of 2-hydroxybutanoic acid to water to hydrogen is 1.0:18:170. It will be found that 1,2-dihydroxybutane is produced using either the copper supported on capped silica or the 15% (w/w) copper on silica catalysts.

Example 13
Effect of Overall Pressure

A 13% (w/w) copper on silica catalyst was prepared according to Example 1. The catalyst was used for the vapor reduction of lactic acid at various pressures. The temperature for the reductions was 180° C. A feed rate of 50% (w/w) lactic acid in water was set to achieve a WHSV of 0.07 $h^{-1}$ across the catalyst. The molar ratio of lactic acid to water to hydrogen was 1:5:146. The overall conversion of lactic acid increased to nearly 100% with greater selectivity of 1,2-propanediol as the overall pressure increased, as shown in Table 8. Table 8 shows that a 100% conversion of lactic acid is possible with a selectivity of 1,2-propanediol of greater than 88%.

Example 14
Stability of Copper on Silica Catalyst

Figure 2:
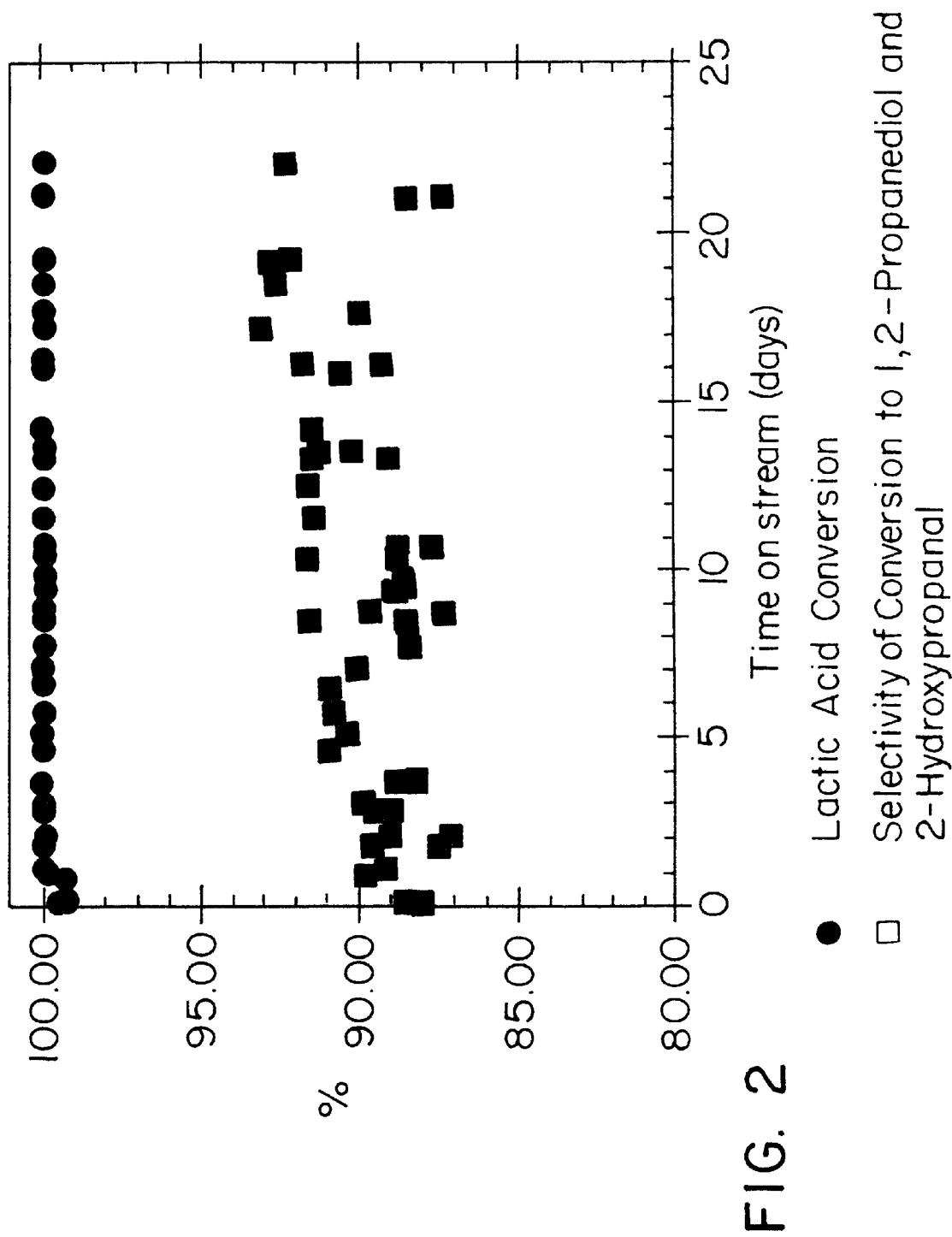
FIG. 2 is a graph showing the stability of a 13% (w/w) copper on silica catalyst over a period of 22 days at a temperature of 200° C. and a total pressure of 3 atm with a WHSV of 0.03 h$^{-1}$ and with a lactic acid:water:hydrogen ratio of 1:20:400. In the graph, ● indicates lactic acid conversion and ■ indicates the selectivity of the conversion to production of 1,2-propanediol and 2-hydroxy-propanal.

A 13% (w/w) copper on silica catalyst was prepared according to Example 1. The catalyst was used for the vapor reduction of lactic acid. The temperature for the reduction was maintained at 200° C. and the WHSV was 0.03 $h^{-1}$ across the catalyst. The molar ratio of lactic acid to water to hydrogen was 1:20:400. The lactic acid was fed to the system as a 20% (w/w) aqueous solution, and the total pressure of the system was 3 atm. FIG. 2 shows the overall conversion of lactic acid and the selectivity of the conversion to produce the desired products (1,2-propanediol and 2-hydroxypropanal). FIG. 2 shows that over a period of 22 days of operation under the conditions described above, the conversion of lactic acid remained at roughly 100% while the selectivity remained at greater than 85%.

TABLE 1

Effects of Copper Content on Lactic Acid Conversion at 1 atm and 200° C. at a Molar Ratio of Lactic Acid:Water:Hydrogen of 1:0.9:35.

| | | Lactic Acid | Selectivity (mole product/mole of LA Converted) × 100 | | | |
|---|---|---|---|---|---|---|
| Catalyst | WHSV[a] ($h^{-1}$) | Conversion (%) | 1,2-Propane-diol | 2-Hydroxy-propanal | Propanoic Acid | n-Propanol and i-Propanol |
| 15% (w/w) Cu/SiO$_2$ | 0.18 | 11 | 78 | 6 | 13 | 3 |
| 10% (w/w) Cu/SiO$_2$ | 0.52 | 5 | 59 | 17 | 23 | 1 |
| 5% (w/w) Cu/SiO$_2$ | 0.52 | 2 | 34 | 29 | 29 | 8 |
| Copper Chromite | 0.28 | 3 | 34 | 35 | 29 | 2 |

[a]WHSV is the Weight Hourly Space Velocity.

TABLE 2

Effects of Water on Lactic Acid Conversion at 1 atm and 200° C. over 15% (w/w) Copper on SiO$_2$.

| | | Lactic Acid | Selectivity (mole product/mole of LA Converted) × 100 | | | |
|---|---|---|---|---|---|---|
| Ratio of LA:H$_2$O:H$_2$ | WHSV[a] ($h^{-1}$) | Conversion (%) | 1,2-Propane-diol | 2-Hydroxy-propanal | Propanoic Acid | n-Propanol and i-Propanol |
| 1:0.8:35 | 0.18 | 11 | 78 | 6 | 13 | 3 |
| 1:18:170 | 0.08 | 14 | 87 | 8 | 4 | 1 |

[a]WHSV is the Weight Hourly Space Velocity.

TABLE 3

Effect of Time on Lactic Acid Conversion at 1 atm and 200° C. over 15% (w/w) Copper on Silica at WHSV of 0.08 h-1. The Molar Ratio of Lactic Acid:Water:Hydrogen was 1:18:170.

| | Lactic Acid | Selectivity (mole product/mole of LA Converted) × 100 | | | |
|---|---|---|---|---|---|
| Time on Stream (hours) | Conversion (%) | 1,2-Propane-diol | 2-Hydroxy-propanal | Propanoic Acid | n-Propanol and i-Propanol |
| 1.5 | 16 | 79 | 7 | 2 | 12 |
| 2.5 | 12 | 84 | 9 | 5 | 3 |
| 3.5 | 16 | 87 | 7 | 4 | 1 |

TABLE 3-continued

Effect of Time on Lactic Acid Conversion at 1 atm and 200° C. over 15% (w/w) Copper on Silica at WHSV of 0.08 h-1. The Molar Ratio of Lactic Acid:Water:Hydrogen was 1:18:170.

| Time on Stream (hours) | Lactic Acid Conversion (%) | Selectivity (mole product/mole of LA Converted) × 100 | | | |
|---|---|---|---|---|---|
| | | 1,2-Propane-diol | 2-Hydroxy-propanal | Propanoic Acid | n-Propanol and i-Propanol |
| 4.5 | 16 | 87 | 8 | 4 | 1 |
| 5.5 | 14 | 87 | 8 | 4 | 1 |

TABLE 4

Effects of Copper Content on Lactic Acid Conversion at 1 atm and 200° C. over Various Supports. Molar ratio of Lactic Acid:Water:Hydrogen was 1:18:170.

| Catalyst | WHSV[a] (h$^{-1}$) | Lactic Acid Conversion (%) | Selectivity (mole product/mole of LA Converted) × 100 | | | |
|---|---|---|---|---|---|---|
| | | | 1,2-Propane-diol | 2-Hydroxy-propanal | Propanoic Acid | n-Propanol and i-Propanol |
| 15% (w/w) Cu/SiO$_2$ | 0.08 | 14 | 87 | 8 | 4 | 1 |
| 15% (w/w) Cu/TMS-capped SiO$_2$ | 0.04 | 7 | 82 | 9 | 3 | 6 |
| 15% (w/w) Cu/γ-Al$_2$O$_3$ | 0.04 | 3 | 43 | 28 | 26 | 2 |
| 5% (w/w) Cu/SiN$_4$ | 0.04 | 1 | 54 | 9 | 9 | 18 |
| 10% (w/w) Cu/ZrO$_2$ | 0.04 | 2 | 0 | 83 | 15 | 2 |

[a]WHSV is the Weight Hourly Space Velocity.

TABLE 5

Effects of WHSV on Copper-Catalyzed Lactic Acid Conversion at 1 atm and 200° C. over 15% (w/w) Copper on Silica. Molar ratio of Lactic Acid and Water was 1:0.9.

| WHSV[a] (h$^{-1}$) | H$_2$ Pressure (Atm) | Lactic Acid Conversion (%) | Selectivity (mole product/mole of LA Converted) × 100 | | | |
|---|---|---|---|---|---|---|
| | | | 1,2-Propane-diol | 2-Hydroxy-propanal | Propanoic Acid | n-Propanol and i-Propanol |
| 0.2 | 0.98 | 6.0 | 68 | 13 | 16 | 1 |
| 0.1 | 0.99 | 7.3 | 75 | 11 | 13 | 1 |
| 0.05 | 0.99 | 19.0 | 85 | 5 | 10 | 0 |
| 0.02 | 0.99 | 36.0 | 84 | 5 | 11 | 0 |

[a]WHSV is the Weight Hourly Space Velocity.

TABLE 6

Effects of H$_2$ Pressure on Copper-Catalyzed Lactic Acid Conversion at 1 atm and 200° C. over 15% (w/w) Copper on Silica at a WHSV of 0.02 h$^{-1}$. Molar ratio of Lactic Acid and Water was 1:0.9.

| H$_2$ Pressure (Atm) | Lactic Acid Conversion (%) | Selectivity (mole product/mole of LA Converted) × 100 | | | |
|---|---|---|---|---|---|
| | | 1,2-Propane-diol | 2-Hydroxy-propanal | Propanoic Acid | n-Propanol and i-Propanol |
| 0.99 | 36 | 83 | 5 | 11 | 0 |
| 0.75 | 21 | 80 | 7 | 13 | 0 |
| 0.50 | 13 | 81 | 7 | 11 | 0 |
| 0.25 | 13 | 73 | 12 | 15 | 0 |

TABLE 7

Effects of Temperature on Copper-Catalyzed Lactic Acid Conversion at 1 atm over 15% (w/w) Copper on Silica at a WHSV of 0.02 h$^{-1}$. Molar ratio of Lactic Acid and Water was 1:0.9, and the H$_2$ partial pressure was 0.99.

| Temperature (° C.) | Lactic Acid Conversion (%) | Selectivity (mole product/mole of LA Converted) × 100 | | | |
|---|---|---|---|---|---|
| | | 1,2-Propane-diol | 2-Hydroxy-propanal | Prop-anoic Acid | n-Propanol and i-Propanol |
| 220 | 60 | 77 | 7 | 15 | 1 |
| 200 | 36 | 83 | 5 | 11 | 0 |
| 180 | 18 | 89 | 4 | 7 | 0 |
| 160 | 13 | 89 | 5 | 6 | 0 |
| 140 | 8 | 91 | 4 | 5 | 0 |

TABLE 8

Effect of Pressure on Lactic Acid Conversion at 180° C. and WHSV of 0.07 h$^{-1}$ over 13% (w/w) Cu/SiO$_2$. Molar ratio of lactic acid, water, and hydrogen was 1:5:146.

| Pressure (Atm) | Lactic Acid Conversion (%) | Selectivity (mole product/mole of LA Converted) × 100 | | | |
|---|---|---|---|---|---|
| | | 1,2-Propane-diol | 2-Hydroxy-propanal | Propanoic Acid | n-Propanol and i-Propanol |
| 1.0 | 74.1 | 54.3 | 22.2 | 22.8 | 0.7 |
| 2.0 | 79.4 | 60.7 | 19.7 | 18.6 | 1.0 |
| 3.0 | 85.0 | 77.2 | 8.2 | 13.6 | 1.0 |
| 4.4 | 95.9 | 82.7 | 5.5 | 10.0 | 1.8 |
| 5.8 | 98.5 | 86.3 | 4.1 | 8.1 | 1.5 |
| 7.1 | 100.0 | 88.2 | 3.3 | 5.9 | 2.6 |

It is understood that the present invention is not limited to the specific applications and embodiments illustrated and described herein, but embraces such modified forms thereof as come within the scope of the following claims.

What is claimed is:

1. A catalytic process, comprising: contacting an organic compound comprising at least one carboxylic acid group and an α-hydroxyl group bonded to a carbon adjacent to the carboxylic acid group with a catalyst comprising zero valent copper in the presence of hydrogen to yield a reduced product, wherein the carboxylic acid group is converted into a second hydroxyl group and the reduced product has at least two hydroxyl groups.

2. The catalytic process according to claim 1, wherein the organic compound is contacted with the catalyst and the hydrogen at a pressure of less than about 25 atmospheres.

3. The catalytic process according to claim 1, wherein the organic compound is contacted with the catalyst and the hydrogen at a pressure of less than about 10 atm.

4. The catalytic process according to claim 3, wherein the organic compound is contacted with the catalyst and the hydrogen at a pressure of from about 3 atm to about 7.1 atm.

5. The catalytic process according to claim 4, wherein the organic compound is contacted with the catalyst and the hydrogen at a pressure of from about 5.8 atm to about 7.1 atm.

6. The catalytic process according to claim 1, wherein the organic compound is contacted with the catalyst and the hydrogen at a hydrogen partial pressure of less than or about 1 atmosphere.

7. The catalytic process according to claim 1, wherein the organic compound is in the vapor phase when it is contacted with the catalyst.

8. The catalytic process according to claim 1, wherein the reduced product is selected from the group consisting of 1,2-propanediol, ethylene glycol, and mixtures thereof.

9. The catalytic process according to claim 1, wherein the organic compound is selected from the group consisting of lactic acid, glycolic acid, and mixtures thereof.

10. The catalytic process according to claim 1, further comprising maintaining the temperature at a range from about 125° to about 250° C. while the organic compound is contacted with the catalyst and the hydrogen.

11. The catalytic process according to claim 1, further comprising maintaining the temperature at a range from about 180° C. to about 250° C.

12. The catalytic process according to claim 11, wherein the organic compound is contacted with the catalyst and the hydrogen at a hydrogen partial pressure of less than or about 4 atmospheres.

13. The catalytic process according to claim 12, wherein the organic compound is contacted with the catalyst and the hydrogen in the presence of water.

14. The catalytic process according to claim 12, wherein the catalyst is a supported catalyst.

15. The catalytic process according to claim 14, wherein the catalyst is supported on silica.

16. The catalytic process according to claim 15, wherein the silica has hydroxyl groups and at least some of the hydroxyl groups on the silica are capped with hydrophobic groups selected from the group consisting of silanes, alkyl groups, and mixtures thereof.

17. The catalytic process according to claim 16, wherein the silanes are trialkylsilanes and the alkyl groups are selected from the group consisting of methyl, ethyl, propyl, butyl, pentyl, hexyl, and mixtures thereof.

18. The catalytic process according to claim 15, wherein the silica has hydroxyl groups and at least some of the hydroxyl groups on the silica are capped with trimethylsilane.

19. The catalytic process according to claim 15, wherein the catalyst is supported on the silica in an amount ranging from about 10 to about 20 percent.

20. A catalytic process, comprising: contacting an organic compound comprising a first hydroxyl group and at least one carboxylic acid group with a catalyst comprising zero valent copper in the presence of hydrogen at a pressure of less than or about 4 atmospheres to yield a reduced product, wherein the at least one carboxylic acid group is converted into a second hydroxyl group and the product has at least two hydroxyl groups.

21. The catalytic process according to claim 20, wherein the organic compound is contacted with the catalyst and the hydrogen at a hydrogen partial pressure of less than or about 1 atmosphere.

22. The catalytic process according to claim 20, wherein the copper is supported on silica.

23. The catalytic process according to claim 22, wherein the copper is supported on the silica in an amount ranging from about 10 to about 20 percent by weight.

24. The catalytic process according to claim 22, wherein the silica has hydroxyl groups and at least some of the hydroxyl groups are capped with a hydrophobic group selected from the group consisting of alkyl groups, silanes, and mixtures thereof.

25. The catalytic process according to claim 22, wherein the organic compound is contacted with the catalyst and the hydrogen in the presence of water.

* * * * *